(12) United States Patent
Greenberg et al.

(10) Patent No.: US 9,061,150 B2
(45) Date of Patent: Jun. 23, 2015

(54) SALIENCY-BASED APPARATUS AND METHODS FOR VISUAL PROSTHESES

(75) Inventors: Robert J. Greenberg, Los Angeles, CA (US); Alan Matthew Horsager, Los Angeles, CA (US); Mark S. Humayun, Glendale, CA (US); Kelly H. McClure, Simi Valley, CA (US); Matthew J. McMahon, Los Angeles, CA (US); Peter Meilstrup, Seattle, WA (US); Neha Jagdish Parikh, Los Angeles, CA (US); Arup Roy, Valencia, CA (US); James D. Weiland, Valencia, CA (US); Chunhong Zhou, Pasadena, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1323 days.

(21) Appl. No.: 12/043,830

(22) Filed: Mar. 6, 2008

(65) Prior Publication Data

US 2009/0112287 A1 Apr. 30, 2009

Related U.S. Application Data

(60) Provisional application No. 60/905,643, filed on Mar. 8, 2007.

(51) Int. Cl.
*A61N 1/36* (2006.01)
*A61F 9/08* (2006.01)
*G06K 9/46* (2006.01)
*G06K 9/60* (2006.01)
*G09B 21/00* (2006.01)

(52) U.S. Cl.
CPC .......... *A61N 1/36046* (2013.01); *G06K 9/4628* (2013.01); *G06K 9/605* (2013.01); *G09B 21/008* (2013.01)

(58) Field of Classification Search
CPC ..... A61N 1/36046; G06K 9/605; G06K 9/46; G06K 9/4604; A61F 9/08
USPC .............. 607/53, 54, 141; 623/6.63; 600/6.63
See application file for complete search history.

(56) References Cited

U.S. PATENT DOCUMENTS

| | | | |
|---|---|---|---|
| 5,109,844 A | 5/1992 | de Juan, Jr. et al. | |
| 5,935,155 A | 8/1999 | Humayun et al. | |
| 6,400,989 B1 | 6/2002 | Eckmiller | |
| 6,458,157 B1 | 10/2002 | Suaning | |
| 2002/0010496 A1 | 1/2002 | Greenberg et al. | |
| 2002/0154833 A1 | 10/2002 | Koch et al. | |
| 2004/0127956 A1* | 7/2004 | Dobelle .......................... | 607/53 |
| 2005/0273141 A1* | 12/2005 | Greenberg et al. ............. | 607/54 |
| 2005/0288733 A1 | 12/2005 | Greenberg et al. | |
| 2006/0106432 A1* | 5/2006 | Sawan et al. .................... | 607/54 |

OTHER PUBLICATIONS

Itti, L., et al., A Model of Saliency-Based Visual Attention for Rapid Scene Analysis, IEEE Transactions on Pattern Analysis and Machine Intelligence, 1998, pp. 1254-1259, vol. 20, No. 11.
Itti, L., et al., A Saliency-Based Search Mechanism for Overt and Covert Shifts of Visual Attention, Vision Research, 2000, pp. 1489-1506.

* cited by examiner

*Primary Examiner* — Tammie K Heller
(74) *Attorney, Agent, or Firm* — Scott B. Dunbar (57) ABSTRACT

The present invention is a saliency-based apparatus and methods for visual prostheses. A saliency-based component processes video data output by a digital signal processor before the video data are input to the retinal stimulator. In a saliency-based method, an intensity stream is extracted from an input image, feature maps based on the intensity stream are developed, plural most salient regions of the input image are detected and one of the regions is selected as a highest saliency region.

21 Claims, 8 Drawing Sheets

*Prior Art*

SALIENCY-BASED APPARATUS AND METHODS FOR VISUAL PROSTHESES

CROSS REFERENCE TO RELATED APPLICATIONS

The present application claims the benefit of priority of U.S. Provisional Patent Application Ser. No. 60/905,643 filed on Mar. 8, 2007, the contents of which are incorporated herein by reference in their entirety.

STATEMENT OF GOVERNMENT GRANT

At least part of the present disclosure is based on work supported by the National Science Foundation under Grant No. EEC-0310723. At least part of the present disclosure was also made with governmental support under grant No. R24EY12893-01, awarded by the National Institutes of Health. The U.S. Government may have certain rights in the present invention.

FIELD

The present disclosure relates to visual prostheses. In particular, it relates to saliency-based apparatus and methods for visual prostheses.

BACKGROUND

Electronic retinal prostheses for treating retinal degenerative diseases such as retinitis pigmentosa (RP) and age-related macular degeneration (AMD) are known. In these diseases, the photoreceptor cells of the retina are affected but other retinal cells remain relatively intact. Hence, the retinal prosthesis electrically activates these remaining cells of the retina to create artificial vision. External components are used to acquire and code image data for transmission to an implanted retinal stimulator.

Figure 1:
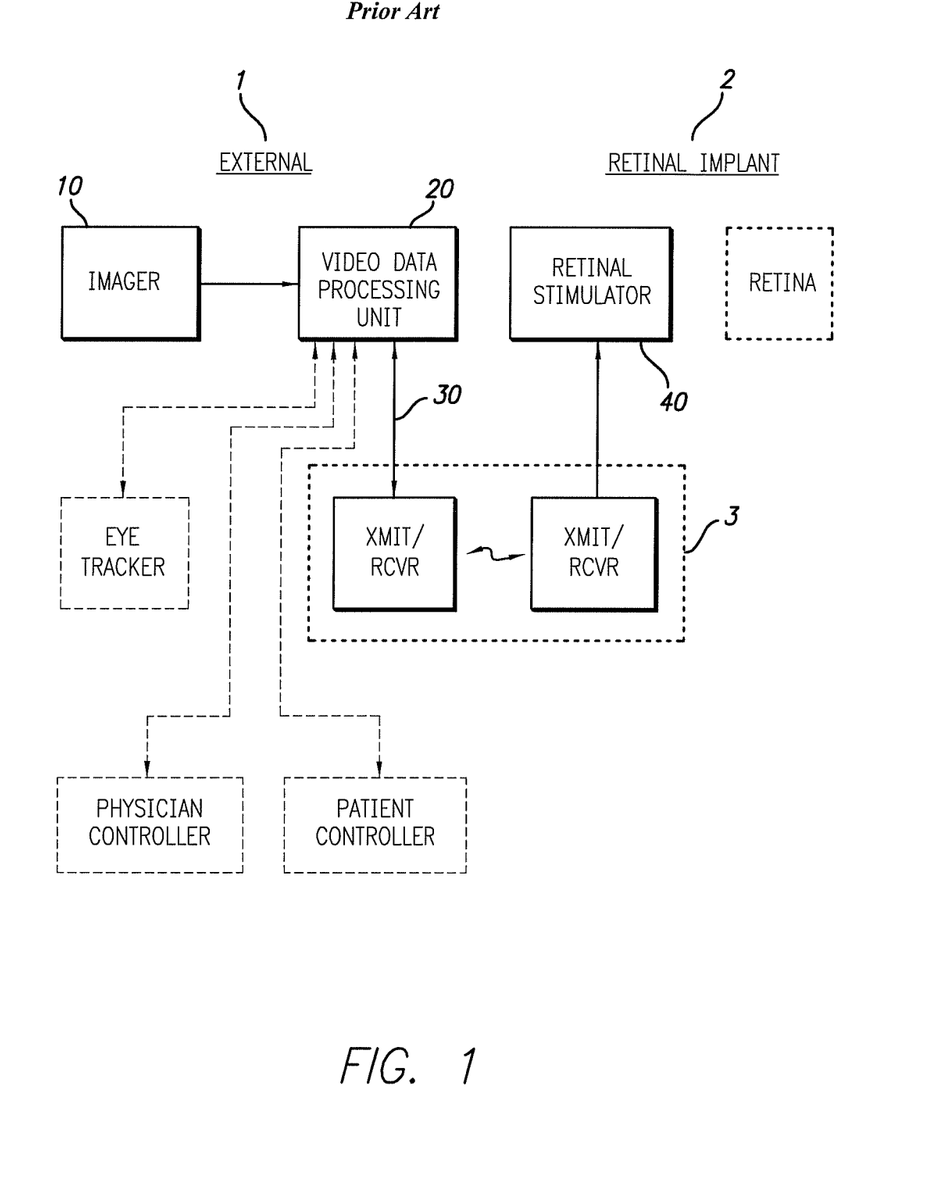
FIG. 1 shows a schematic representation of the main components of a visual prosthesis.

FIG. 1 shows a schematic representation of the main components of a visual prosthesis taken from U.S. published patent application 2005/0288735, incorporated herein by reference in its entirety. In particular, the external portion (1) of the visual prosthesis comprises an imager (10), e.g., a video camera, to capture video in real time, and a video data processing unit (20) comprising a Digital Signal Processor (DSP) to process video data and then send output commands (30) for a retinal stimulator to be implanted on the retina of a patient. Currently, the video camera (10) outputs images having resolution of about 640×480 to the DSP in real time. The DSP takes in these images and does image processing on each of these input frames. The processing rate can be of about 3 to 30 image frames per second depending on the processing method or algorithm. The output (30) of the DSP is to be sent to the telemetry block (3) of the retinal prosthesis system, which will not be explained here in detail.

The electrode grid of the retinal stimulator (40) to be implanted in the eye is currently of size 10×6. This implies that the resolution of the image output (30) from the DSP contained in the video data processing unit (20) is to be 10×6. A 10×6 size electrode grid array significantly reduces the field of vision that can be offered to a patient. Currently, such field of view is about 20 degrees. With a restricted field of vision, the patient has to scan the scene in front with head movements and find out the region that looks significant or worth giving attention to.

Saliency methods or algorithms are known in the art. Generally speaking, a saliency method treats different parts of the same image differently, focusing only on relevant portions or sections of that image. A saliency algorithm per se is known from Itti et al (see "A model for saliency-based search visual attention for rapid scene analysis" by Laurent Itti, Christof Koch and Ernst Niebur, IEEE Transactions for Pattern Analysis and Machine Intelligence, Vol 20, No 11 Nov 1998 and "A saliency-based search mechanism for overt and covert shifts of visual attention" by Laurent Itti and Kristof Koch, both of which are incorporated herein by reference in their entirety). In particular, Itti et al use a visual-attention model which is based on an early primate visual attention model and aims at finding the most salient region of an image frame at any given instant. According to Itti et al's algorithm, saliency at a given location is determined primarily by how different the location is from its surround in color, orientation, motion, depth and so on.

Figure 2:
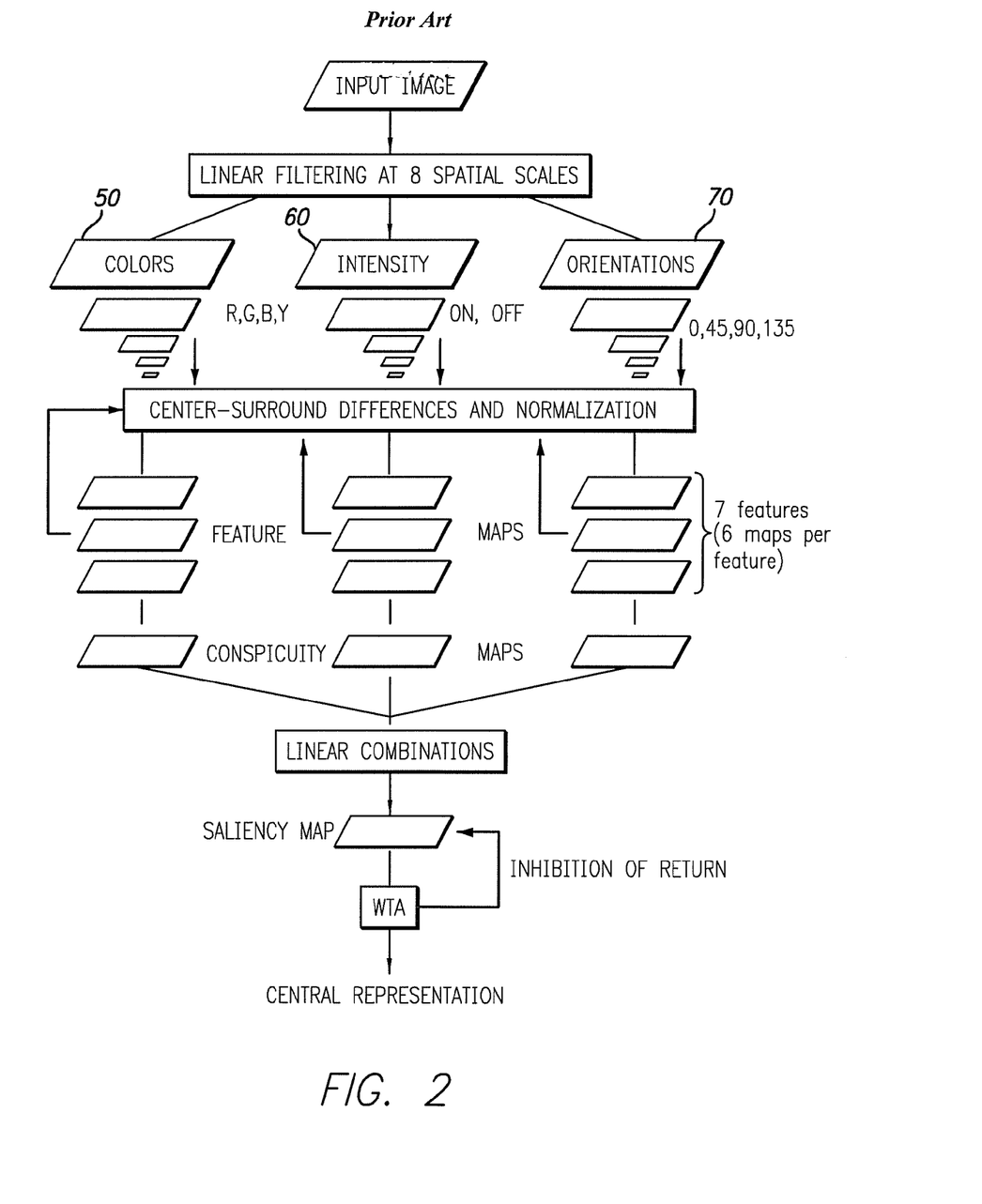
FIG. 2 shows a general overview of Itti et al's saliency algorithm.

FIG. 2 shows a general overview of Itti et al's saliency algorithm. In particular, the algorithm concentrates on the color (50), intensity (60) and orientation (70) information in any given image frame to calculate the most conspicuous location of an input image. 7 streams of information like intensity, Red-Green color, Blue-Yellow color and orientations at 0, 45, 90 and 135 degrees are extracted from the input image. Image pyramids with 9 levels are constructed for each of the information streams. Feature-maps for the center-surround structure are developed by taking the difference between the finer and coarser scales of the pyramids. Three conspicuity maps are constructed by summing the feature-maps of the three kinds of information after normalization. Normalization is a process to combine different modalities like intensity, color and orientation. Normalization helps to promote the maps having strong peaks and suppress the maps having comparable peaks and to bring feature-maps of the different information streams at the same level in order to linearly sun them to form the final saliency map. The saliency conspicuity map is constructed by summing the conspicuity maps for color, intensity and orientation, thus obtaining a topographically arranged map that represents visual saliency of the input image. A region surrounding the pixel with the highest gray-scale value is taken as the most salient region.

SUMMARY

According to a first aspect, a visual prosthesis is provided, comprising: an image processor to process video data from an imager; a visual stimulator to stimulate visual neurons on a patient; and a saliency-based component to process the video data before the video data are input to the visual stimulator, the saliency-based component being configured to apply a saliency algorithm on the video data.

According to a second aspect, a method of providing video data to a subject with an implanted visual stimulator is provided, the implanted visual stimulator associated to an image processor processing video data from an input image, comprising: extracting only an intensity stream from the input image; developing feature maps based on the intensity stream; detecting a plurality of most salient regions of the input image based on the feature maps; selecting one salient region of the most salient regions as a highest saliency region; and providing highest saliency region information to the subject According to a third aspect, an apparatus for providing stimulation signals to a visual stimulator is provided, comprising: a saliency map generator to process a video input coming from a camera image; a downsampling component to downsample saliency map resolution to visual stimulation resolution; and a stimulation component to provide stimulation signals based on the downsampled saliency map resolution.

According to a fourth aspect, an apparatus for providing stimulation signals to a visual stimulator is provided, comprising: a saliency map generator to process a video input coming from a camera image and generate a saliency map; and a stimulation component to provide stimulation signals to the visual stimulator based on the saliency map generated by the saliency map generator.

According to a fifth aspect, a method for providing stimulation signals to a visual stimulator is provided, comprising: generating a saliency map of an input image; separating the input image into multiple regions according to saliency values of the saliency map; and separating stimulation of the multiple regions through the visual stimulator in time in accordance with a rastering process.

According to a sixth aspect, a method of providing video data to a subject with an implanted visual stimulator is provided, the implanted visual stimulator associated to a processor processing video data from an input image, the method comprising: detecting salient regions of the input image through a discrete wavelet transform process.

According to a seventh aspect, an apparatus for providing video data to a subject with an implanted visual stimulator is provided, the implanted visual stimulator associated to a processor processing video data from an input image, the apparatus comprising: a module configured to detect salient regions of the input image through a discrete wavelet transform process.

According to an eighth aspect, an apparatus for providing video data to a subject with an implanted visual stimulator is provided, the implanted visual stimulator associated to a processor processing video data from an input image, the apparatus comprising: a module configured to detect salient regions of the input image through a discrete wavelet transform process operating on two-dimensional data, the module comprising a plurality of levels of filters, each level comprising a first sub-level operating on data in a first dimension and a second sub-level operating on data in the second dimension.

According to a ninth aspect, a method of providing video data to a subject, comprising: receiving video data having a first resolution; processing the video data in accordance to a saliency method to obtain processed video data having a second resolution, lower than the first resolution, the processing being adapted to prefer peripherally located video data to centrally located video data once the peripherally located video data is more salient than the centrally located video data; and sending the processed video data to a visual stimulator implanted on the subject.

According to a tenth aspect, a visual prosthesis is provided, comprising: a camera sensitive to ultraviolet light; a visual stimulator to stimulate visual neurons on a patient; and means to process video data output from the camera, the video data including data corresponding to the ultraviolet light, before the video data are input to the visual stimulator.

Further aspects and embodiments of the present disclosure will become clear to the person skilled in the art upon reading of the specification, drawings and claims of the present application.

DETAILED DESCRIPTION

The present disclosure applies a "saliency" method or algorithm to a visual prosthesis. In particular, the saliency algorithm, method or block will further process the video data processed by the DSP before they are input to the 10×6 electrode grid. For example, the saliency block can operate in parallel with the DSP. Alternatively, or in addition to that, the saliency block or module can be inside the DSP, and/or operate before or after the DSP. According to further embodiments, the saliency block can also operate on an input image together with a (field-programmable-gate-array) FPGA or with an application-specific integrated circuit (ASIC). In the next paragraphs, an exemplary embodiment where the saliency block is provided after a DSP will discussed. However, the person skilled in the art will understand that other embodiments are possible, also on the basis of what stated in the present paragraph.

Figure 3:
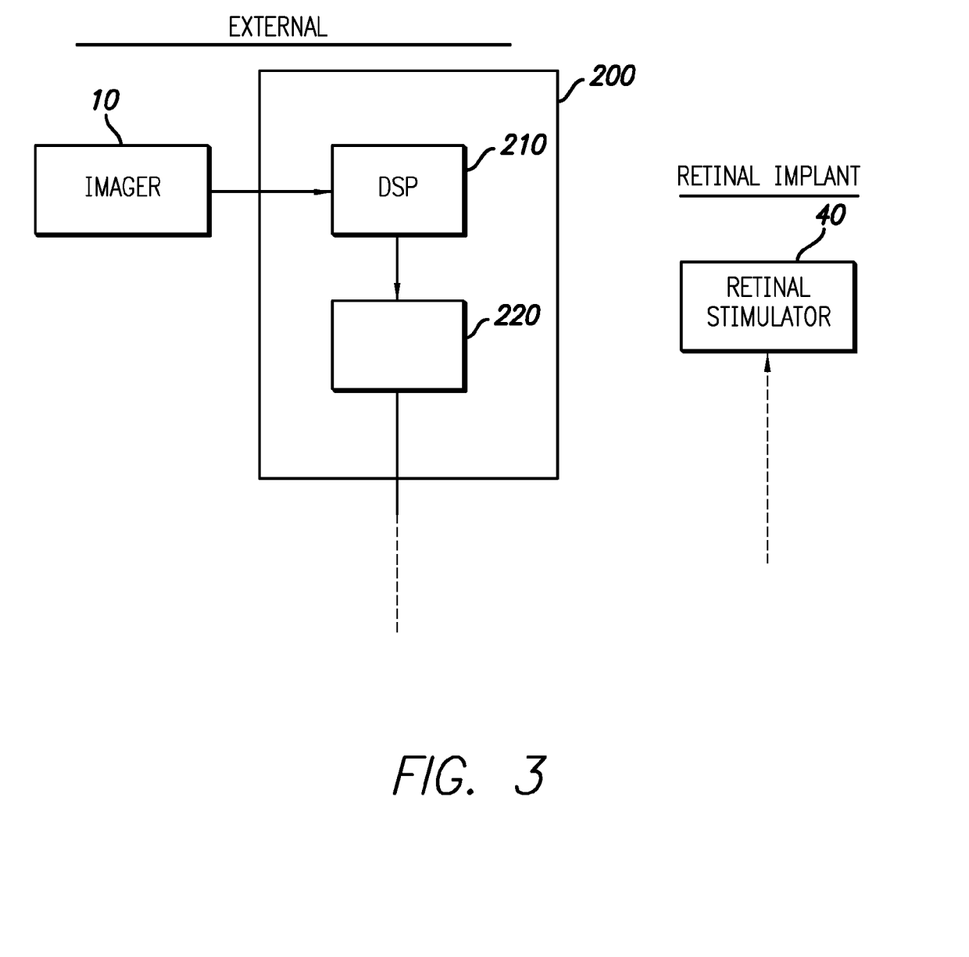
FIG. 3 shows a video data processing unit in accordance with an embodiment of the present disclosure.

According to an embodiment of the present disclosure, a saliency algorithm or method is applied to a visual prosthesis system like the one shown in FIG. 1 above. By way of example and not of limitation, FIG. 3 shows a video data processing unit (200) comprising a DSP (210) and a saliency module (220). As soon as the DSP (210) processes the video data coming from the imager (10), the saliency module (220) further processes the output of the DSP (210), in accordance with Itti et al's algorithm or the methods later explained in the present application. The person skilled in the art will also understand that while FIG. 3 shows a saliency module (220) right after the DSP (210), other embodiments are possible so long as the saliency module (220) is placed after the DSP (210) and before the retinal stimulator (40). More generally, the retinal stimulator (40) can be any kind of visual stimulator, for example a stimulator stimulating the cortical regions of a patient. As to the DSP (210), one possible choice is the TMS320 DM642 video and imaging processor from Texas Instruments. Such embodiment is well suited for testing purposes. However, for practical use, DSPs of small size and running on low power may be better suited to be used in the present disclosure. In other words, the digital signal processor (210) should run on a limited amount of power compliant with power limits of devices operating on visual prostheses. Moreover, as also explained above, FPGAs and/or ASICs can be provided instead or together with DSPs.

Applicants have implemented Itti et al's saliency algorithm shown in FIG. 2 above to allow regions of interest to be detected in the peripheral visual field of a subject, thus giving audio or video cues to the subject to look in the direction of the region of interest. An image location is considered "salient" if it contains different luminance, color, texture, differently oriented structure, motion or other features than the surrounding regions. Salient locations should be emphasized in the visual presentation on the visual prosthesis device stimulation, so they can be easily picked up by the subject. On the basis of salient regions, the patients divert their gaze in the salient region instead of scanning an entire scene. Therefore, in accordance with the present disclosure, saliency is used to aid patients search and look for important objects in their environment and to simulate a scanning environment, thus achieving a good agreement between the gaze points of a subject (which imply those points are salient for the subject in a given image) and the salient points detected by the algorithm.

The applicants have noted that application of the above algorithm with respect to a retinal prosthesis recipient lies in the detection of objects or obstacles. Some of the steps performed by applicants are shown in FIG. 4.

In particular, with this application in mind, the applicants have set the processing rate of the algorithm on the DSP to meet about 3-5 frames per second. The applicants have also noted that Itti et al's algorithm with 7 streams of information from the intensity, color and orientation of an image is computationally very expensive for the DSP to run it at 3-5 frames per second. However, the applicants have noted that the intensity information is essentially contrast information and is contained in just 1 out of the 7 streams being processed by the saliency algorithm, i.e. the intensity stream. Considering this, the applicants have selected to use only the intensity stream for saliency detection, as shown in step S1 of FIG. 4.

Figure 4:
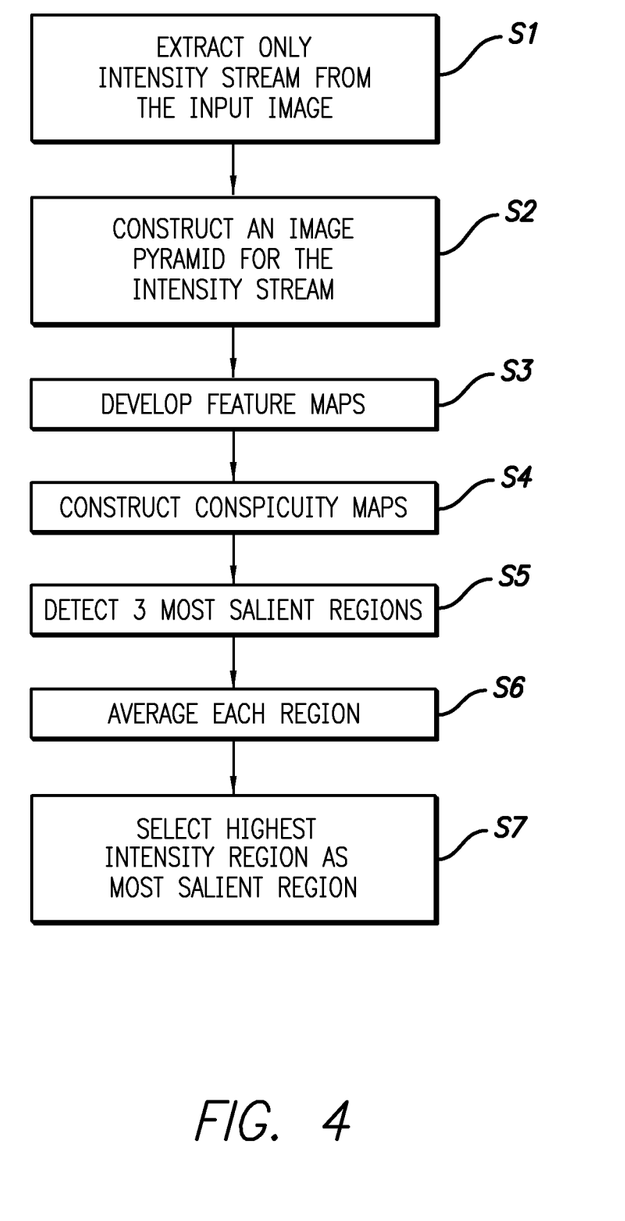
FIG. 4 shows some steps of a saliency method according to an embodiment the present application.

Moreover, in order to detect the most salient region, instead of taking the highest intensity pixel and a region around it as in the algorithm of FIG. 2, applicants first detect 3 most salient regions, as shown in step S5 of FIG. 4. The three regions can be detected by rank-ordering the regions in the image (as done in Itti et al, for example) and then by selecting the three highest-ranked regions. These regions undergo simple averaging (step S6) and then the highest intensity region is selected as the most salient region (step S7). This is done in order to avoid extremely small regions with a few high grayscale pixels to be detected over larger regions with more pixels but slightly lesser grayscale values. This is also done so that smaller but brighter regions in an image do not overshadow larger but slightly less intense regions as these could potentially be the more relevant regions to a subject.

There are two types of normalization processes proposed by Itti et al, which are iterative normalization and max normalization. Normalization is one of the most expensive routines in the Itti et al algorithm. For this reason, applicants have opted, in one embodiment of the present disclosure, to not perform any kind of normalization. Such disadvantage is overcome by the fact that, in accordance with what explained above, 3 most salient regions are detected and the best of them is chosen. Not performing normalization allows a higher amount of frames per second to be processed, as shown in the following table, where the time is expressed in seconds and applicant's method is run on a DM642 720 MHz DSP.

|  | Iterative Normalization | Max Normalization | No Normalization |
| --- | --- | --- | --- |
| Gaussian Pyramids | 0.1262 | 0.1276 | 0.1276 |
| Center-surround maps | 0.0273 | 0.0248 | 0.0249 |
| Normalization at different levels of the pyramids | 0.9919 0.1261 0.0163 | 0.0579 0.0209 0.0108 | 0.0008 |
| Saliency marker | 0.0141 | 0.0208 | 0.0175 |
| Entire algorithm | 2.5237 | 0.5092 | 0.1955 |
| Frames/sec | 0.3962 | 1.9639 | 5.1151 |

Time to Complete Normalization in Seconds

The saliency method described above has been implemented on MATLAB® software. Simulink® software from Mathworks, Inc. has been used to target the DSP processor and to load and run the code to and from the DSP.

According to a further embodiment of the present disclosure, a method of computing and presenting a saliency map to a subject is described. The saliency map can be obtained through the basic Itti et al's algorithm, or other methods, like the one shown in FIGS. 3 and 4 above.

According to Itti et al's algorithm, as already explained above, image features such as luminance, color, and orientation are computed from a scene. A center-surround and normalization process computes the feature maps based on the filter results. Feature maps are integrated into conspicuity maps based on the feature categories. A linear process integrates these into an explicit saliency map. The saliency map is the starting point of the method according to this further embodiment.

Figure 5:
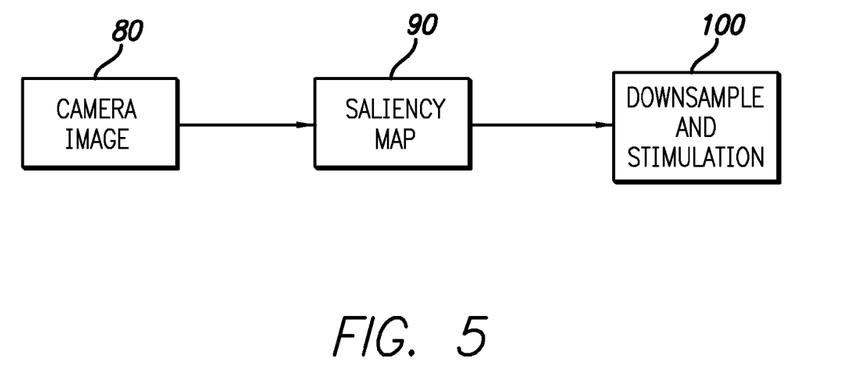
FIGS. 5-7 shows schematic diagrams of saliency map-based stimulation approached.

According to a first aspect of this further embodiment, the computed saliency map is sub-sampled and presented directly to a subject by encoding high saliency locations with brighter stimulation (or vice versa). As shown in FIG. 5, a saliency map (90) generated after processing a video input coming from a camera image (80) is down-sampled to the resolution of the electrode array (e.g., a 10×6 electrode array) and presented to the subject by way of stimulation (100). Incidentally, in all of the embodiments of the present disclosure, the camera can also be sensitive to infrared (IR), ultraviolet (UV), ultrasound and X-ray spectra. In particular, the inventors have found that using heat (IR) as a saliency factor is beneficial. By way of example, anything that is dangerously hot is highly salient. Further, people and most animals will show up in IR and are salient. Moreover, visual prostheses cameras as such, sensitive to UV light, are also provided.

Figure 6:
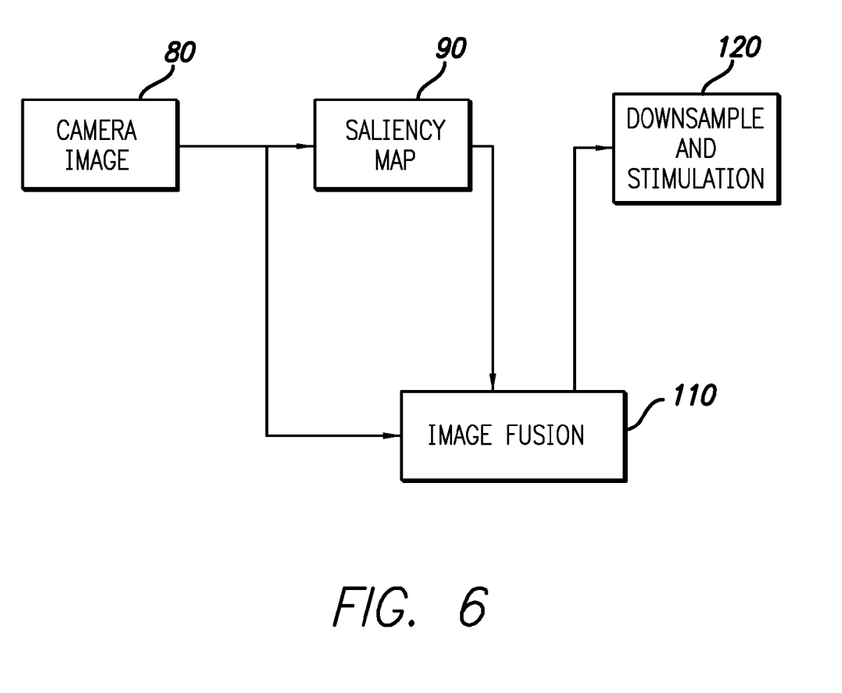

According to a second aspect of this further embodiment, the computed saliency map is used to modulate the stimulation, as shown in FIG. 6. For example, image contrast in high saliency areas can be enhanced, while low saliency image areas can be smoothed. Such aspect can be combined with the use of one or more image fusion algorithms (110). For example, using wavelet fusion, an image can be decomposed into wavelet domain. The wavelet coefficient, then can be multiplied or scaled using the corresponding saliency value. The reconstruction from such modulated coefficients will have higher contrast at the higher saliency areas and will be sub-sampled to the resolution of the electrode array and presented to the subject by way of stimulation (120).

Figure 7:
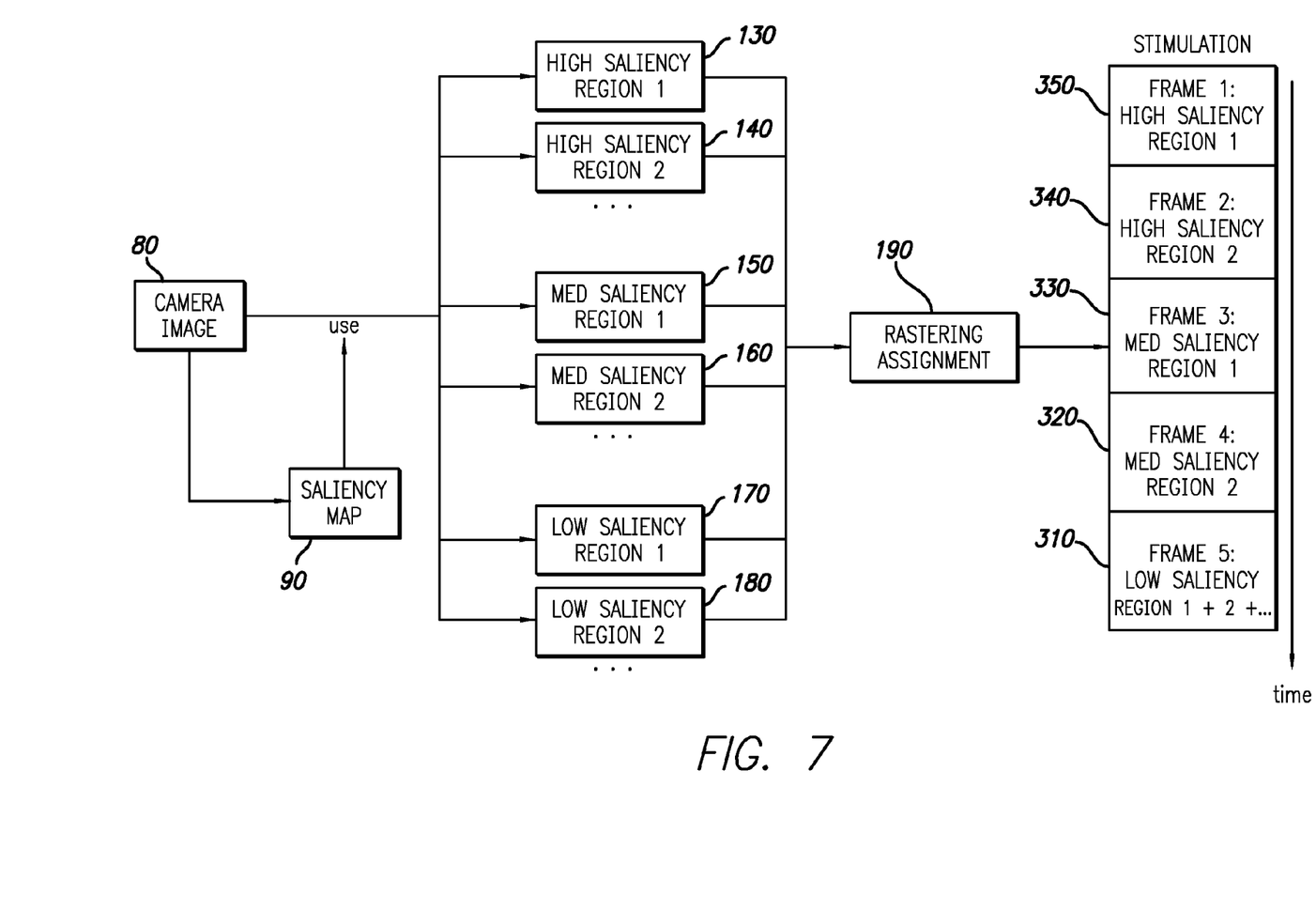

According to a third aspect of this further embodiment, the computed saliency map can be used to determine the stimulation sequence and assignment in a rastering scheme. In a rastering stimulation pattern, each group of electrodes is assigned to a unique stimulation temporal pattern. When presented to a new image, electrodes that correspond to higher saliency regions can be stimulated earlier and separately in the rastering pattern. Thus, when these electrodes are stimulated, there will be more contrast since other electrodes are not stimulated. On the other hand, for the low saliency regions, the corresponding electrodes will be stimulated later. Higher saliency means higher probability of being stimulated alone, which helps to promote more contrast as shown, for example, in FIG. 7 which depicts an exemplary presentation strategy according to this third aspect. With reference to such figure, the input camera image (80) is separated into multiple regions (130)-(180) according to the saliency value. A rastering assignment module (190) separates the stimulation of regions (130)-(180) in time. Low saliency regions (170), (180) are grouped together (310), while high saliency regions (130), (140) and medium saliency regions (150), (160) are stimulated independently of each other (320)-(350). Moreover, according to this third aspect, certain regions of the image can be chosen not to be stimulated to the subject if they fall below a certain saliency threshold. Since not all electrodes will be stimulated, this approach helps lowering the power consumption.

According to a yet further embodiment of the present application, a saliency algorithm or method alternative to the one devised by Itti et al and alternative to the one shown in FIGS. 3 and 4 of the present application is shown. According to this method, a discrete wavelet transform (DWT) is used to extract information about size and location of visual features such as points and edges in the image. The DWT is a wavelet transform for which the wavelets are discretely sampled. A wavelet is a mathematical function used to divide a given function or signal into different frequency components and study each component with a resolution that matches its scale.

Figure 8:
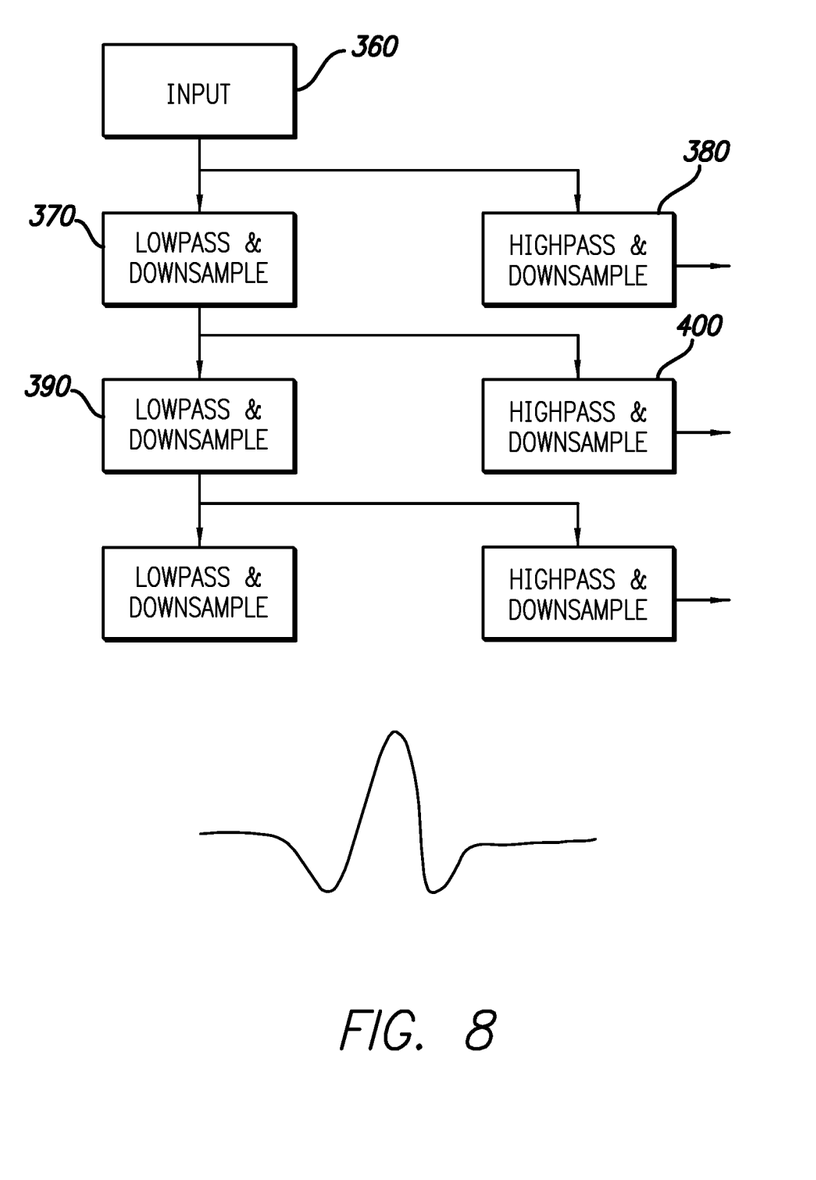
FIGS. 8 and 9 shows saliency methods based on a discrete wavelet transform.

As shown in FIG. 8, the DWT of an input signal (360) is calculated by passing it through a series of filters. The samples are simultaneously passed to a first level lowpass filter (370) and a first level highpass filter (380). After filtering, the filter outputs are downsampled by two. The output of the first level highpass filter (380) will provide first level coefficients, while the output of the first level lowpass filter (370) is input to second level lowpass (390) and highpass (400) filters, and the process is repeated.

In accordance with such embodiment, the DWT allows extraction of information about the size and location of visual features such as points and edges in the image. The image data (360) is input as an array of pixels of intensity values. As shown in FIG. 8, the DWT is recursively defined on one-dimensional data as a pair of filter-and-downsample operations. The highpass operation extracts small scale information from the signal. The lowpass operation eliminates small scale content before downsampling. As further shown in FIG. 8, the lowpass image can undergo further filter-and-downsample operations, resulting in a "ladder" of information at multiple scales. With each step down the ladder, the frequency content represented is one octave lower, and the sampling rate is one half that of the next higher level, thus leading also in this case to an O(n) complexity. Exemplary filter coefficients (LP) for the lowpass modules are LP=[⅛ ½ ¾ ½ ⅛]. Exemplary filter coefficients (HP) for the highpass modules are HP=[−½ 1 −½]. The various operations can be easily performed with bit-shifts and adds, giving raise to the wavelet shown at the bottom of FIG. 8.

Figure 9:
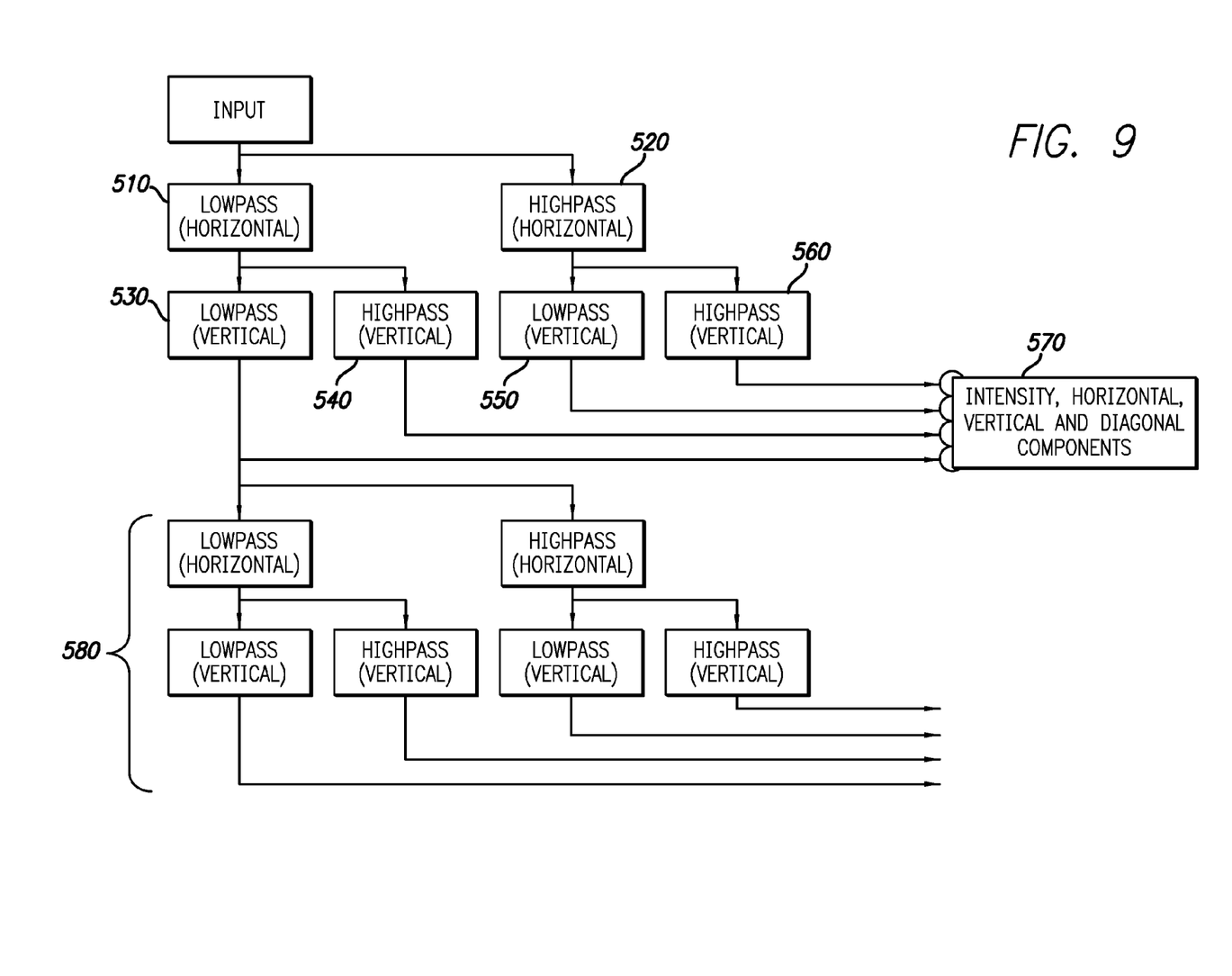

FIG. 9 shows application of the DWT in a two-dimensional environment. A lowpass/downsample (410) and highpass/downsample (420) first level operation is initially done in a horizontal direction. The outputs of both the horizontal highpass and horizontal downpass block are then input to two separate vertical lowpass/downsample blocks (430), (440) and to two separate vertical highpass/downsample blocks (450), (460). The person skilled in the art will understand that the initial operation can also be done in a vertical/horizontal fashion instead of horizontal/vertical as shown. This two-dimensional extension of the DWT implicitly does orientation filtering, so that post-filtering steps are unnecessary.

The approach described above divides the image into four components which contain information from vertical edges, horizontal edges, diagonal edges, and a lowpass intensity approximation (470). Such approximation is sent to a second level (480) having a horizontal/vertical (or vertical/horizontal) configuration identical to the first level, and iteration is performed, similarly to the one-dimensional environment.

After a DWT of the image is done, the result is rectified, to eliminate oscillations and show the power present at each combination of location and scale. Data from each scale are then convolved with a difference-of-gaussians filter which deemphasizes areas of consistent spectral content (thus filtering the maps to suppress areas of similar energy) while emphasizing areas which stand out from their surroundings. Finally, the inverse wavelet transform is taken with a non-oscillatory filter to normalize the maps. A lowpass filter is used to reconstruct both the lowpass and highpass components. In this way, oscillatory features are replaced with a general elevation of the signal, showing areas where high frequency spectral content is localized. The salient locations will be identified as local maxima of the output signal. In particular, the local maxima will be located and sorted based on their proximity to other maxima.

Use of DWT in place of the oriented Laplacian pyramid of Itti et al and elimination of complex-valued filtering gives an approximate 4× increase in speed over Itti et al. Optimizations in other filtering operations can provide additional speedups. For example, a 61×61 image can be processed in about 50,000 operations, making the method viable for real-time implementation on a processor such as a DSP.

According to a further embodiment of the present disclosure, video information having a first resolution is processed to information having a second, lower, resolution by way of a saliency method, and then sent to a visual stimulator on a patient. The saliency method will also allow "peripheral" information of an image to be processed by a patient once such information is salient, and not only "central" information of the image (which would be the usual outcome of a higher-to-lower resolution processing). According to a yet further embodiment, the way of sending such information to the patient can include selective activation of electrodes (e.g., edge electrodes only) or even activation of some "cues", such as a tactile cue or an auditory cue. Therefore, according to this embodiment, saliency is used to cue different regions in the peripheral visual field.

More specifically, the field of view of a camera adapted to be used with a visual prosthesis is greater than the field of view of the prosthesis (20 degrees). Thus only the central 20 degrees of information from each image/video frame would be stimulated whereas the peripheral information falling outside the 20 degrees central field of view will be lost. On the other hand, the saliency module according to the present disclosure will take in the entire video/image frame and process it for salient regions. If there are salient regions falling outside the central 20 degree field of view, the patient could be alerted to the presence of salient regions using video/audio/tactile cues. The cues will be in one of the 8 directions: right, left, top, bottom, top-left, bottom-left, top-right and bottom-right with respect to the central field of view. Thus recipients can move their head and divert their attention to important things in the periphery. In particular, audio cues would utter the directions of the cues, video cues would mean stimulating peripheral electrodes corresponding to the cueing directions.

According to another embodiment of the present disclosure, instead of running continuously on the DSP at a certain frame rate, the saliency algorithm could be used to give cues to subjects when they demand them (saliency "on demand"). This could help patient familiarize themselves with unknown environments etc and to know the area around them when they wish to do so. Running saliency on a continuous basis might put challenging computational loads on the DSP and at the same time might be too confusing for patients because in that case, they would be continuously receiving cues which could make things more complicated for them to comprehend.

According to a yet further embodiment of the present disclosure, saliency is applied to multiple images. In this environment, a moving object is almost always more salient than a stationary object, so that one could also cue on motion. In fact, that is how natural vision works: the peripheral vision is adapted to cue on motion. One sees motion "in the corner of her eye" and she naturally looks at it. In the same way, motion cue can be combined with the "peripheral" embodiment to obtain a system that acts more like natural vision.

In accordance with a further embodiment of the disclosure, pattern recognition can also be added as a feature. In particular, a table of salient stored patterns (e.g., a chair or a car) is stored in the visual prosthesis and compared with the salient features identified by the saliency module, so that each time there is a match the patient is alerted to that pattern.

In summary, according to some embodiments of the present disclosure, saliency-based apparatus and methods for visual prostheses are disclosed. A saliency-based component processes video data output by a digital signal processor before the video data are input to the retinal stimulator. In a saliency-based method, an intensity stream is extracted from an input image, feature maps based on the intensity stream are developed, plural most salient regions of the input image are detected and one of the regions is selected as a highest saliency region.

Accordingly, what has been shown are saliency-based methods in visual prostheses. While the methodology has been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

What is claimed is:

1. A visual prosthesis comprising:
an image processor to process video data from an imager, including a saliency module for separating the video data into a plurality of video streams, including the saliency module selecting at least one video stream from a group containing luminance, color, texture, differently oriented structure, and motion and producing a selected at least one video stream;
a visual stimulator to stimulate visual neurons on a patient;
the saliency module further including a saliency-based component to process the selected at least one video stream before the video data are input to the visual stimulator, the saliency-based component being configured to apply a saliency algorithm to the selected at least one video stream and alter the video data according to the saliency algorithm; and
means for selectively activating electrodes to provide a cue to a visual prosthesis subject as to which region, including regions outside the field of view of the subject, is most salient.

2. The visual prosthesis of claim 1, wherein the image processor and the saliency-based component are part of a video data processing unit.

3. The visual prosthesis of claim 1, wherein the image processor and the saliency-based component operate in parallel.

4. The visual prosthesis of claim 1, wherein the image processor is a digital signal processor (DSP), a field-programmable gate array (FPGA) or an application-specific integrated circuit (ASIC).

5. The visual prosthesis of claim 1, wherein the saliency-based component operates on the video data after or before the image processor.

6. The visual prosthesis of claim 1, wherein the saliency-based component is a software component.

7. The visual prosthesis of claim 1, wherein the image processor runs on a limited amount of power compliant with power limits of devices operating on visual prostheses.

8. The visual prosthesis of claim 1, wherein the image processor has a processing rate of 3 to 30 frames per second.

9. The visual prosthesis of claim 8, wherein the image processor has a processing rate of 3 to 5 frames per second.

10. The visual prosthesis of claim 1, wherein the saliency-based component, only processes an intensity stream of the video data.

11. The visual prosthesis of claim 1, wherein the saliency-based component is adapted to be turned on and turned off on demand.

12. The visual prosthesis of claim 11, wherein turning on and turning off the saliency-based component on demand is effected by a patient using the visual prosthesis.

13. The visual prosthesis of claim 1, wherein the video data pertain to multiple images.

14. The visual prosthesis of claim 13, wherein the saliency-based component cues on motion.

15. The visual prosthesis of claim 1, wherein the imager is sensitive to visible light, infrared, ultraviolet, X-ray spectra, or ultrasound.

16. The visual prosthesis of claim 1, further comprising a pattern recognition component.

17. The visual prosthesis of claim 16, wherein the pattern recognition component comprises a table of salient stored patterns for comparison with the results of the saliency component.

18. The visual prosthesis according to claim 1, wherein the plurality of video streams includes intensity.

19. The visual prosthesis according to claim 1, wherein the plurality of video streams includes color.

20. The visual prosthesis according to claim 1, wherein the plurality of video streams includes orientation.

21. The visual prosthesis according to claim 1, wherein the plurality of video streams includes movement.

* * * * *